(12) United States Patent
Muller

(10) Patent No.: US 7,220,384 B2
(45) Date of Patent: May 22, 2007

(54) WASHING AND EXTRACTING HEAD FOR MICROPLATE WASHING APPLIANCE AND CORRESPONDING APPLIANCE

(75) Inventor: Franck Muller, Strasbourg (FR)

(73) Assignee: Bio-Rad Pasteur, Marnes la Coquette (FR)

( * ) Notice: Subject to any disclaimer, the term of this patent is extended or adjusted under 35 U.S.C. 154(b) by 341 days.

(21) Appl. No.: 10/469,958

(22) PCT Filed: Mar. 7, 2002

(86) PCT No.: PCT/FR02/00832

§ 371 (c)(1),
(2), (4) Date: Sep. 8, 2003

(87) PCT Pub. No.: WO02/070135

PCT Pub. Date: Sep. 12, 2002

(65) Prior Publication Data

US 2004/0089330 A1 May 13, 2004

(30) Foreign Application Priority Data

Mar. 8, 2001 (FR) .................................. 01 03182

(51) Int. Cl.
*B32B 5/02* (2006.01)
(52) U.S. Cl. .......................... 422/63; 422/99; 422/100; 422/101; 422/64; 436/180
(58) Field of Classification Search ............ 422/63–64, 422/99–101; 436/180
See application file for complete search history.

(56) References Cited

U.S. PATENT DOCUMENTS

| 4,493,896 A | 1/1985 | La Motte, III et al. |
| 4,635,665 A | 1/1987 | Namba et al. |
| 4,909,992 A | 3/1990 | Bjorkman |
| 5,951,783 A * | 9/1999 | Kontorovich et al. ......... 134/21 |

FOREIGN PATENT DOCUMENTS

| EP | 0 903 181 | 3/1999 |
| FR | 2 536 313 | 5/1984 |

* cited by examiner

*Primary Examiner*—Jill Warden
*Assistant Examiner*—Jyoti Nagpaul
(74) *Attorney, Agent, or Firm*—Young & Thompson

(57) ABSTRACT

Apparatus and washing and extracting head for an apparatus designed to wash microplates. The head is mobile above the microplate(s) in treating position and comprises an alignment of dispensing needles or tubes and suction needles or tubes associated in pairs, the number of the two types of needle pairs being equal to the number of wells per column or per row and the spacing between two adjacent pairs being equal to the spacing between two adjacent wells of the same column or row. The suction needles, and the parts of the consecutive suction and/or recovery circuit, have a passage cross sectional diameter not less than the largest transverse dimension of the sample supports present in the wells and the head comprises or co-operates with elements retaining the microplate to be washed or preventing it from being lifted, at least during the suction extraction phase.

13 Claims, 3 Drawing Sheets

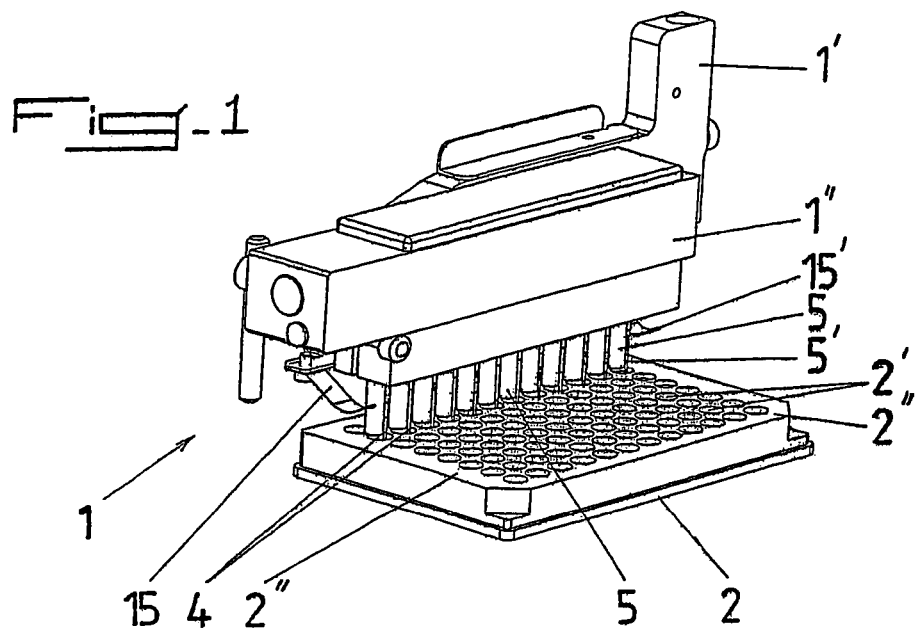
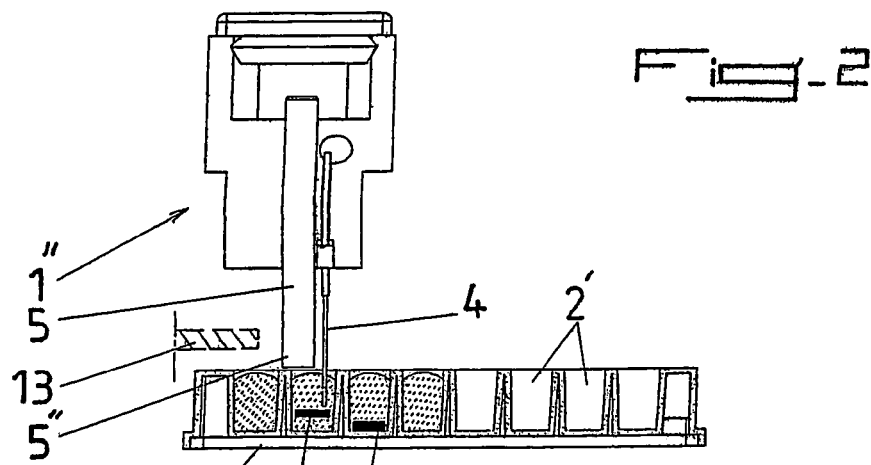
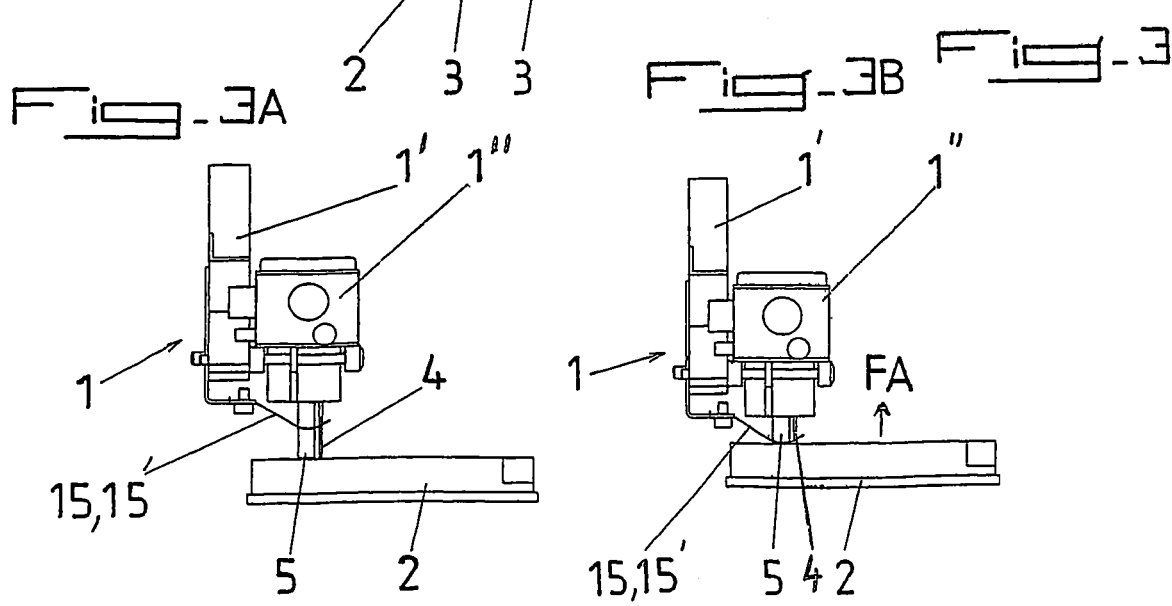

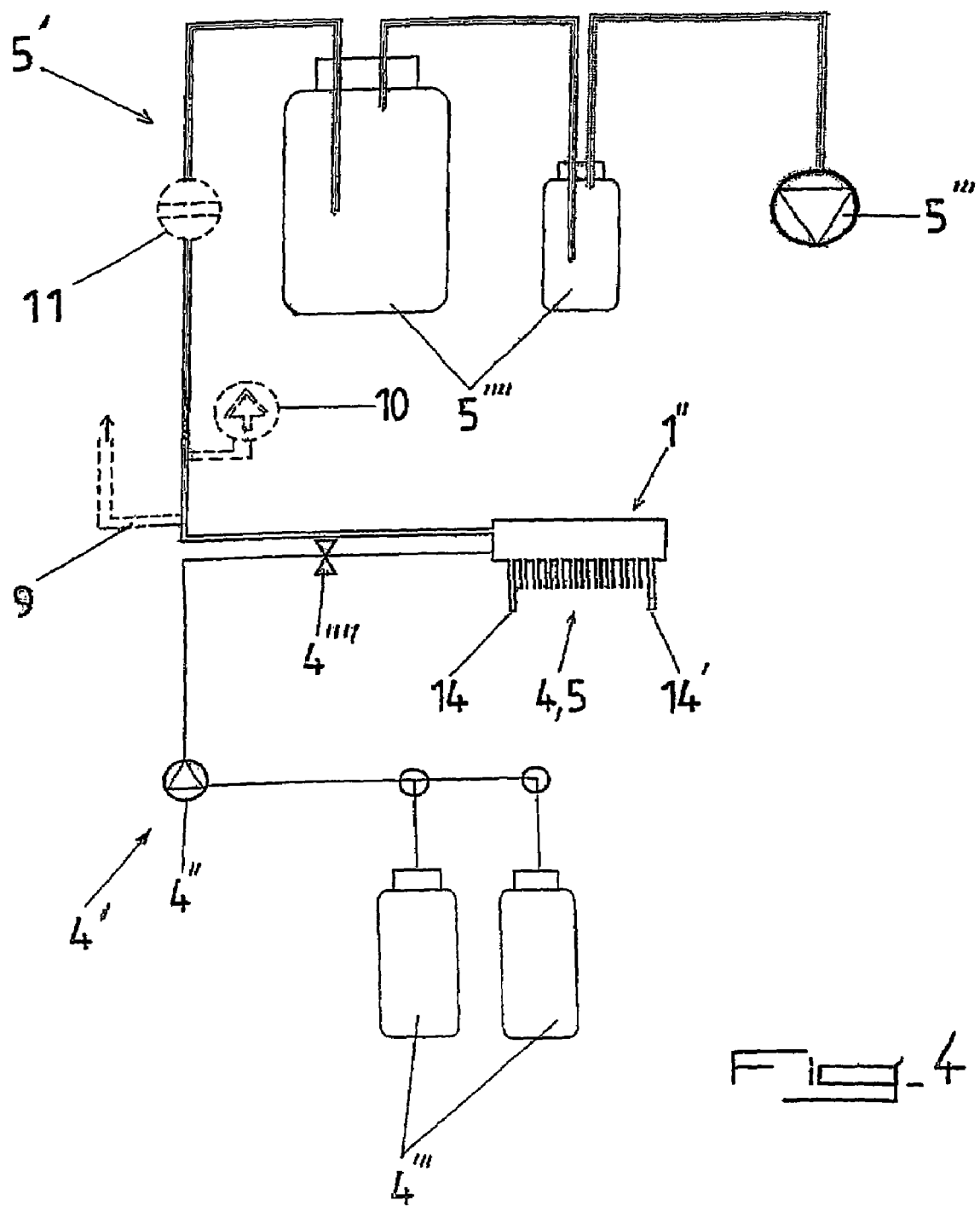
Fig_4

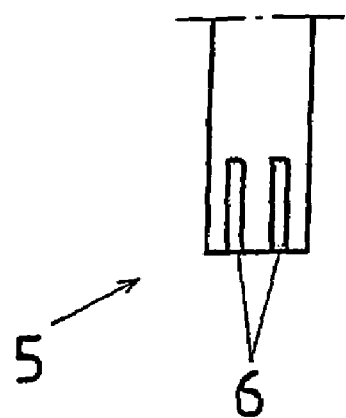
Fig_5
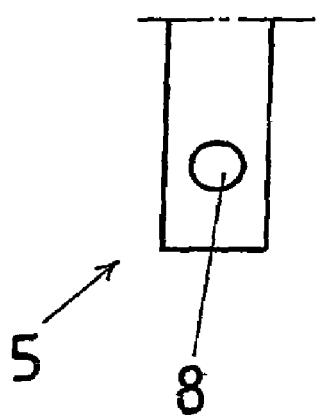
Fig_6
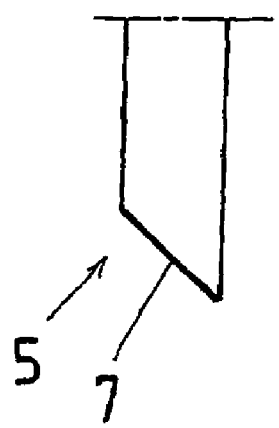
Fig_7

WASHING AND EXTRACTING HEAD FOR MICROPLATE WASHING APPLIANCE AND CORRESPONDING APPLIANCE

BACKGROUND OF THE INVENTION

The present invention relates to the field of diagnostic techniques and medical tests by means of microplates, and more particularly the automatic treatment of such plates, and has for its object a washing and extraction head for a washing robot, as well as an apparatus or a microplate washing station comprising such a head.

At present, numerous medical tests have been carried out in batteries by means of microplates in the form of a support plate of plastic material provided with a plurality of reinforcements in the form of wells each receiving a sample to be analyzed, said analysis wells being generally arranged in a flat matrix arrangement of rows and columns that are mutually perpendicular.

Before analysis, these microplates must be treated for the preparation and handling of the different samples in a form (in solution) suitable for the tests and/or for the operative manipulations to be carried out and, after removal or analysis, it is necessary to clean said wells by washing, possibly several times, and rinsing.

For this purpose, said microplates are placed in or brought into a washing robot or a washer principally constituted by a support adapted to receive said microplates and by a removable washing and extraction head associated with fluid supply and removal circuits.

The support of the microplates and the head can be moved relative to each other in at least one straight direction disposed in the plane of the microplate in the treatment position and in a direction perpendicular to said plane.

Such a head is, in known manner, movable above the microplate or plates in the treatment position and generally comprises a row of needles or distribution tubes connected to a liquid supply circuit for washing and/or rinsing and a row of needles or suction tubes connected to an evacuation and/or recovery circuit, with each needle of the first type being associated a needle of the second type with an offset in the direction of movement of relative translation between said head and said microplates in the course of treatment of these latter, a number of pairs of needles of the two types being equal to the number of wells per column or per row, or to a fraction of this number, and a spacing between two adjacent pairs of needles being equal to the spacing between two adjacent wells of the same column or row, or to a multiple of this spacing.

Automatic microplate washing apparatus or stations provided with such a head, are also known and there can, for example, on this subject, be cited the automatic washer known under the name LAVEUR LP40 of the company ADIL INSTRUMENTS.

These known washers and heads are well adapted for the treatment of microplates whose wells receive the usual samples in liquid or dissolvable solid form.

However, for neonatal diagnosis, there exists a technique of removal of particular samples on blotting paper. The sample is deposited on the blotting paper by direct removal from the heel of the newborn. This method facilitates the sending of samples to a central analysis laboratory (sent in an envelope, not a specimen tube).

This type of test is very widespread in Europe. For analysis, the laboratory recovers the blood specimen to be analyzed by cutting out one or several discs of standard dimension from the sheet of blotting paper impregnated with blood (3.2 mm or 4.5 mm diameter). The sample discs to be analyzed are then deposited in the wells of a microplate. The addition of a buffer (dilution solution) permits dissolving the specimen to be analyzed. After prolonged incubation, the paper disc must be withdrawn from the microplate to be able to continue the qualitative analysis. The plate thus follows a conventional cycle of washing and then reading at the end of diagnosis.

At present, in the automatic processes for treating microplates, there must be two different devices for carrying out the phases of extraction of the discs and washing of the microplate, so as to avoid plugging the suction circuit for the liquid of the washing apparatus.

Thus, the extraction of the discs is carried out by or on an extractor for sucking up the discs one by one. After extraction, the user verifies that there remain no more discs at the bottom of the microplate, and then places the microplate in the washer.

The result is high cost and large space requirement, because of the use of two different apparatus and a substantial prolongation of the duration of the washing phase, the present extractors operating with a single needle (well by well) and the operator having to transfer manually the microplate from one apparatus to the other.

An alternative method consists in returning the microplate manually and to tap it against a flat surface, which constitutes a delicate operation and requires careful verification on the part of the operator.

Finally, for the two alternative methods of extraction set forth above, the risks of plugging the suction needles for liquid of the washing apparatus cannot be entirely overcome, which should give rise to frequent requirements for maintenance and lead to poor washing of the wells that could result in subsequent false analyses.

SUMMARY OF THE INVENTION

The present invention has for its object to overcome or avoid the mentioned drawbacks, whilst not modifying fundamentally the construction of the washing heads and the present automatic washers.

To this end, it has for its principal object a washing and extraction head for automatic apparatus for washing microplates, of the mentioned type, and characterized in that its suction needles, as well as the portions of the consecutive suction and/or recovery circuit, have a cross-section of passage diameter at least equal to the greatest transverse dimension of the specimen supports, for example the diameter of the discs, and in that said head comprises or coacts with at least one means ensuring the holding of the microplate to be washed or preventing its rising, at least during the phase of extraction by suction.

The invention also has for its object an apparatus or automatic station for washing analysis microplates with wells, that can contain sample supports of fibrous material, said microplates being wedged in a treatment position on a support plate movable in translation in at least one direction, the apparatus or station being characterized in that it comprises a washing and extraction head as described above.

BRIEF DESCRIPTION OF THE DRAWINGS

The invention will be better understood from the following description, which relates to preferred embodiments and variations, given by way of non-limiting example, and explained with reference to the accompanying schematic drawings, in which:

FIG. 1 is a perspective view of a preferred embodiment in two parts of the washing head according to the invention, provided with means for holding the microplate according to a modified embodiment of the invention;

FIG. 2 is a cross-sectional and transverse elevational view of the microplate and of the collector forming a part of the washing head shown in FIG. 1;

FIGS. 3A and 3B are side elevational views, on a different scale, of the washing head shown in FIG. 1, respectively in the retracted and in the extended position with the introduction of suction needles into a row or column of wells;

FIG. 4 is a schematic diagram of the fluid circuits connected to the washing and extraction head according to the invention, showing various modifications of reduction/regulation means for the suction force, and, FIGS. 5 to 7 show, in side elevation and on a different scale, a suction needle forming a portion of the washing and extraction head according to different modified embodiments of the invention.

DETAILED DESCRIPTION OF THE PREFERRED EMBODIMENTS

As shown in FIGS. 1 to 7 of the accompanying drawings, the washing and extraction head 1 is movable above the microplate or microplates 2 in the treatment position and comprises a row of needles or distribution tubes 4 connected to a supply circuit 4' for washing and/or rinsing liquid and a row of suction needles or tubes 5 connected to a circuit 5' for evacuation and/or recovery, with each needle 4 of the first type being associated a needle 5 of the second type with an offset in the direction of movement of relative translation between said head 1 and said microplates 2 in the course of treatment of these latter, the number of needle pairs 4 and 5 of the two types being equal to the number of wells 2' per column or per row, or to a fraction of this number, and the spacing between two adjacent pairs 4 and 5 of needles being equal to the spacing, or to a multiple of the spacing, between two adjacent wells 2' of the same column or row.

Each microplate 2 comprises a plurality of analysis wells 2' open in their upper portion and arranged according to a matrix arrangement in rows and columns perpendicular to each other, said wells 2' being particularly adapted to receive sample supports 3 of fibrous material of a predetermined size, in particular of disc shape.

The supply circuit 4' comprises a pump 4'' for circulating washing and rinsing solutions removed from corresponding bottles 4''' and distributed to the needles 4 through a supply control valve 4''''.

The evacuation and/or recovery circuit 5' comprises a source of controlled vacuum 5''' (for example a high flow rate vacuum pump) adapted to create a vacuum at the level of the needles 5 through (mounted as a wash bottle) at least one bottle 5'''', preferably two, mounted in series, for recovery of the waste (solution+discs).

According to the invention, the suction needles 5, as well as the portions of the circuit 5' for suction and/or consecutive recovery, have a cross-section of passage diameter at least equal to the greatest transverse dimension of the sample supports 3, for example at least equal to the diameter of the discs, and said head 1 comprises or coacts with at least one means 6; 7; 8; 9; 10; 11; 12; 13; 14; 14'; 15, 15' ensuring the holding of the microplate 2 to be washed or preventing its rising or movement, in a controlled manner, at least during the phase of extraction by suction.

Given the intensity of the suction force generated, in combination with the high suction flow rate at the suction needles 5 and the nature of the contact between said needles and the walls of the wells 2', said microplate 2 will be raised during the suction phase and/or the rising of the head 1, in the absence of such suitable compensation means.

These compensation means could have a permanent action during all the duration of the treatment phase or a time-wise limited action and synchronized with the suction.

To proceed to the extraction of the discs 3 or the fibrous waste remaining after prolonged immersion, the needles 5 are rapidly lowered into the wells 2' of the microplate 2. The air flow generated by the vacuum pump 5''' in the needles 5 will permit the evacuation of the liquid contained in the wells 2' and at the same time the evacuation of the discs 3 or waste contained in the washing liquid. The liquid and the discs will be trapped in the first of the waste bottles 5'''' mounted in series in the circuit 5'.

According to a first general modified embodiment of the invention, shown particularly in FIGS. 2 to 7 of the accompanying drawings, the means for preventing the rising of the microplates 2 is constituted by a means or an assembly of coacting means 6; 7; 8; 9; 10; 11; 12; 13; 14, 14' reducing or regulating the suction force of the suction needles 5 individually, collectively or for only certain of said needles 5.

As shown in FIGS. 5 to 7 of the accompanying drawings, the means individually reducing the suction force of the suction needles 5 can consist in a specific physical configuration of said needles 5 providing a parasitic loss during suction, such as a free end 5'' of the body of the needle 5 provided with at least one slot 6, a beveled end 7 of the needle or else a needle body provided with at least one radial calibrated perforation 8.

The means collectively reducing the suction force of the suction needles 5 could also consist (see FIG. 4) of a means for regulating the suction force of the level of the evacuation and/or recovery circuit 5', such as a calibrated leak 9, a valve 10 limiting the suction or an electrovalve 11 for temporarily cutting off the suction flow.

The calibrated leak 9, if desired also controlled by a valve, could as the case may be, be directly provided in the head 1.

According to a particular embodiment of the first modified embodiment of the invention, the means reducing collectively, or for certain ones, the suction force of the suction needles 5, can consist in a means 13; 14, 14' limiting the depth of introduction of at least certain needles 5 into the wells 2', particularly preventing the contact of at least certain needles 5 with the bottoms or the sidewalls of the wells of the corresponding wells 2'.

This limiting means could for example be present in the form of an abutment 13, physical or electronic, which is to say a detector of position or movement, whose measurement is evaluated by the control and management unit controlling the operation of the washer (compare FIG. 2).

As shown in FIG. 4 of the accompanying drawings, the limiting means can also be present in the form of at least one suction needle 5, preferably two needles 14, 14', located at opposite ends of the row of suction needles 5, having a length greater than the other needles 5 and projecting relative to these latter.

In the course of the descent of the row of needles 5 into the wells 2', the needles 14, 14' will also serve as onboard abutments, blocking the other needles 5 at a predetermined distance from the bottoms of their respective wells 2'.

According to another particular form of the first modified embodiment of the invention, not shown in the accompanying drawings, the means collectively reducing the suction force of the needles 5 can consist in a sequencer permitting, in an alternative way, simultaneous suction of only a fractional group of the assembly of needles 5, the needles 5 of the different groups being preferably distributed in a uniform manner along the row.

According to a second modified general embodiment of the invention, the means ensuring the holding of the microplate 2 to be treated, consists in a means or assembly of means exerting a pressure force 15, 15' or tractive force in a direction opposite to the direction of the suction force FA produced by the needles 5, at least during the suction phases and the beginning of withdrawal or retraction of said suction needles 5 for their removal from the treated wells 2'.

According to a particular embodiment of this second general modification, the assembly of means exerting a temporary pressure force on the microplate 2 to be treated, can consist of passive or active compliant means 15, 15' carried by the washing and extracting head 1 and coming to bear against the microplate 2 on the edges or opposite edge regions 2" of this latter, beyond the region occupied by the wells 2'.

The active compliant means can for example be constituted by a pair of actuators controlled in synchronism with the movement of the washing and extraction head 1 (not shown).

The passive compliant means can themselves be present in the form of a pair of resiliently deformable elements 15, 15' such as leaf springs or helicoidal springs, if desired provided with bearing shoes.

As to the particularly preferred embodiment of the invention, shown in FIGS. 1 to 3 of the accompanying drawings, the head 1 is comprised by a support 1' movable in a controlled manner in a direction perpendicular to the plane of the microplate 2 in the treatment position and by a hollow body 1" forming a collector, carrying the distribution needles 4 and suction needles 5 and ensuring their connection to their respective fluid circuits 4' and 5', said collector 1" being mounted on or in the movable support 1' with blockage in a plane parallel to the plane of the microplate 2 in the treatment position and with the possibility of relative translation in the direction perpendicular to said plane, from a low holding position, the assembly of the temporary holding means of the microplates 2 being present in the form of two leaf springs 15, 15' of flattened S or Z shape, fixed on the movable support 1' and coming to bear against edge regions 2" of the microplate 2 to be treated with a bearing force at least equal to the collective suction force of the suction needles 5 before said needles 5 arrive at the position of maximum introduction into the wells 2' and remaining thus bearing at least until the suction needles 5 have left said maximum introduction position, preferably until the latter have been entirely withdrawn from their respective wells 2'.

Such a construction of washing head, without extraction needles 5 and resilient means 15, 15', is already known from the ADIL INSTRUMENTS company under the mark "MANIFOLD LP40 WITH SUPPORT"

During descent of the head 1, there will be seen a simultaneous movement downward of the support 1' and of the collector 1" until the suction needles 5 come to bear against the bottoms or the sidewalls of the wells 2' of a row or column of the microplate 2.

The support 1' could continue its descending movement, without supporting or driving the collector 1", this latter then resting with its own weight in the wells 2'.

After completion of the extraction phase, the support 1' begins its ascending movement and raises, after the body of the collector 1" has come to bear against a support abutment 1', said collector 1" until the needles 4 and 5 have been completely withdrawn from the wells 2' with their lower free ends located above the upper surface of the microplate 2 in the treatment position.

According to another particular form of the second modification of the invention, not shown in the accompanying drawings, the means exerting a tractive force on the microplate 2 can be provided by suction means creating a suction effect or vacuum, at least temporarily, below the microplate 2 to be treated, such as a support plate perforated at the region of reception of the microplates 2 and subjected to vacuum applied subjacently.

Finally, according to a third general modification of the invention, not shown in the accompanying drawings, the means ensuring the holding of the microplate 2 to be treated can consist of a wedging and lateral gripping device, if desired associated with a fixed or retractable piece that comes into lateral gripping or engagement.

This third modification could, for example, be implemented by an increase in the pressure force of the present blade for positioning the microplate 2 (to carry out holding by lateral gripping), by holding by adhesion (increasing the adherence between the blade and the microplate) or by a vertical retention of the microplate by fixed holding means (an assembly of shapes) or retractable holding means forming a portion of the support or plate receiving said microplates or forming a part of another mechanical subassembly of the washing apparatus.

Although described above as independent modifications, those skilled in the art will easily understand that it can also be provided to combine or associate two or more of the different modified embodiments or of the holding means or the means for preventing raising of the microplate 2, if desired different forms of modification of a same recited variation.

The washing and extraction head 1 thus permits providing numerous advantages relative to the present state of the art, namely, the absence of the risk of plugging (particularly when carrying out several washing/extraction passes), rapidity of operation (treatment by rows or columns), the absence of manual intervention between the extraction phases of the discs 3 and washing, small size (practically no supplemental size relative to a conventional washing head) and desirable cost relative to two heads mounted in two different devices (one for extraction and one for washing).

The present invention also has for its object an apparatus or automatic washing station for microplates for analysis with wells that contain sample supports of fibrous material, said microplates being wedged in a treatment position on a support plate movable in translation in at least one direction, which apparatus or station is characterized in that it comprises a washing and extraction head as described above.

Of course, the invention is not limited to the modifications of embodiment described and shown in the accompanying drawings. Modifications remain possible, particularly as to the construction of the various elements or by substitution of technical equivalents, without thereby departing from the scope of protection of the invention.

The invention claimed is:

1. Washing and extraction head for an apparatus or robot for washing microplates, said microplates comprising a plurality of analysis wells open at their upper part and arranged in a matrix arrangement in rows and columns perpendicular to each other, said wells being adapted to receive sample supports of fibrous material of a predetermined size, said head being movable above the microplates in a treatment position and comprising:

a row of distribution needles or tubes connected to a circuit for the supply of at least one of washing and rinsing liquid; and a row of suction needles or tubes connected to an evacuation/recovery circuit, with each distribution needle being associated with a suction needle with an offset in the direction of movement of relative translation between said head and said microplates when said microplates are being washed, the number of pairs of needles being equal to the number of wells per column or row, or to a fraction of this number, and a spacing between two adjacent pairs of needles being equal to the spacing between two adjacent wells of the same column or row, or to a multiple of this spacing, wherein said head comprises a support movable in a controlled manner in a direction perpendicular to the plane of the microplates in the treatment position and by a hollow body forming a collector, carrying the distribution needles and suction needles and ensuring their connection to their respective fluid circuits, wherein the suction needles, as well as portions of the consecutive suction/recovery circuit, have a cross-sectional passage diameter at least equal to the largest transverse dimension of fibrous sample supports to be evacuated, and wherein said head comprises or coacts with at least one means for holding the microplates to be washed or preventing the microplates from rising, at least during the phase of extraction by suction, wherein the means for holding the microplates consists of passive compliant means or active compliant means carried by the washing and extraction head and bearing against edge regions of the microplates with a bearing force at least equal to a collective suction force of the suction needles, wherein the means for holding the microplates to be treated consists of a means or an assembly of means exerting a pressure force or traction in a direction opposite the direction of the suction force (FA) produced by the needles, at least during the suction phases and at the beginning of withdrawal or of retraction of said suction needles for their removal from the treated wells, wherein said means for holding the microplates bears against the microplates on edges or opposite edge regions of the microplates, beyond a region occupied by the wells, wherein said collector is mounted on or in the movable support with blockage in a plane parallel to the plane of the microplates in the treatment position and with the ability for relative translation in the direction perpendicular to said plane, from a low holding position, the assembly of temporary holding means for the microplates being present in the form of two leaf springs in the form of flattened S or Z, fixed on the movable support and wherein said suction needles arrive at their position of maximum introduction into the wells and remain in a bearing relation at least until said suction needles have left said maximum introduction position.

2. Head according to claim 1, wherein the means preventing the rising of the microplates is constituted by a means or an assembly of cooperating means reducing or regulating the force of suction of the suction needles, individually, collectively or for only certain ones of said needles.

3. Head according to claim 2, wherein the means individually reducing the suction force of the suction needles consists in a specific physical configuration of said needles providing a parasitic leak during suction, such as a free end of the needle body provided with at least one slot, a beveled end of the needle, or a needle body provided with at least one calibrated radial perforation.

4. Head according to claim 2, wherein the means collectively reducing the suction force of the suction needles consists in a means for regulating the suction force at the level of the evacuation and/or recover circuit, such as a calibrated leak, a valve limiting the vacuum or an electrovalve for temporarily cutting off the suction flow.

5. Head according to claim 2, wherein the means collectively or for certain ones reducing the suction force of the suction needles consists of a means limiting the depth of introduction of at least certain needles in the wells, particularly preventing the contact of at least certain needles with the bottoms or the sidewalls of the corresponding wells.

6. Head according to claim 5, wherein the limiting means is present in the form of a physical or electronic abutment.

7. Head according to claim 5, wherein the limiting means is present in the form of at least one suction needle located at the opposite ends of the row of suction needles, having a length greater than the other suction needles and projecting relative to the other suction needles.

8. Head according to claim 2, wherein the means collectively reducing the suction force of the needles consists in a sequencer permitting in an alternative manner a simultaneous suction only at the level of a fractional group of the assembly of needles, preferably distributed uniformly along the row.

9. Head according to claim 1, wherein the active compliant means are constituted by a pair of actuators controlled in synchronism with the movement of the washing and extraction head.

10. Head according to claim 1, wherein the passive compliant means are present in the form of a pair of resiliently deformable elements such as leaf springs or helicoidal springs.

11. Head according to claim 1, wherein the means exerting a tractive force on the microplate is formed by a suction means creating a suction or vacuum effect, at least temporarily, below the microplate to be treated.

12. Head according to claim 1, wherein the means ensuring the holding of the microplate to be treated consists of a wedging and lateral gripping device, if desired associated with a fixed or retractable piece to come into gripping or lateral engagement.

13. Apparatus or automatic station for washing analysis microplates with wells that can contain sample supports of a fibrous material, said microplates being blocked in a treatment position on a support plate movable in translation in at least one direction, wherein said apparatus or automatic station comprises a washing and extraction head according to claim 1.

* * * * *